US011647806B2

(12) United States Patent
Roh et al.

(10) Patent No.: US 11,647,806 B2
(45) Date of Patent: May 16, 2023

(54) SMART INSOLE AND BALANCE ENHANCEMENT DEVICE COMPRISING THE SAME

(71) Applicants: Samsung Electronics Co., Ltd., Suwon-si (KR); SNU R&DB Foundation, Seoul (KR)

(72) Inventors: Se-Gon Roh, Suwon-si (KR); Jeongin Moon, Seoul (KR); Prabhat Pathak, Seoul (KR); Jooeun Ahn, Seoul (KR); Changhyun Roh, Suwon-si (KR); Youngbo Shim, Suwon-si (KR)

(73) Assignees: Samsung Electronics Co., Ltd., Gyeonggi-do (KR); SNU R&DB FOUNDATION, Seoul (KR)

( * ) Notice: Subject to any disclaimer, the term of this patent is extended or adjusted under 35 U.S.C. 154(b) by 315 days.

(21) Appl. No.: 16/916,765

(22) Filed: Jun. 30, 2020

(65) Prior Publication Data

US 2021/0085014 A1    Mar. 25, 2021

(30) Foreign Application Priority Data

Sep. 25, 2019  (KR) .......................... 10-2019-0118121

(51) Int. Cl.
*A43B 3/34* (2022.01)
*A43B 13/14* (2006.01)
(Continued)

(52) U.S. Cl.
CPC ................ *A43B 3/34* (2022.01); *A43B 13/14* (2013.01); *A61B 5/1038* (2013.01); *A61B 5/112* (2013.01); *A61B 5/6807* (2013.01)

(58) Field of Classification Search
CPC .. A43B 3/34; A43B 13/14; A43B 3/38; A43B 17/00; A43B 7/24; A43B 7/1415;
(Continued)

(56) References Cited

U.S. PATENT DOCUMENTS 8,308,665 B2 * 11/2012 Harry .................... A43B 19/00
                                                        600/595
8,676,541 B2 *  3/2014 Schrock ............... G06F 3/0334
                                                        702/188
(Continued)

FOREIGN PATENT DOCUMENTS

CN          203105800 U     8/2013
KR       10-2017-0019175 A  2/2017
(Continued)

OTHER PUBLICATIONS

Peter Novak, et al., "Effect of step-synchronized vibration stimulation of soles on Gait in Parkinson's disease: a pilot study", Journal of NeuroEngineering and Rehabilitation, May 4, 2006, doi:10.1186/1743-0003-3-9.

(Continued)

*Primary Examiner* — Sean P Dougherty
(74) *Attorney, Agent, or Firm* — Harness, Dickey & Pierce, P.L.C.

(57) ABSTRACT

Provided is a smart insole including a support layer; a plurality of pressure sensors provided to the support layer and configured to sense a pressure; a plurality of vibrators provided to the support layer and configured to generate a vibration; and a controller configured to determine a center of pressure (COP) based on a pressure sensed by each of the plurality of pressure sensors and to control the plurality of vibrators based on a positional relationship between a setting point and the COP.

19 Claims, 17 Drawing Sheets

(51) Int. Cl.
*A61B 5/103* (2006.01)
*A61B 5/11* (2006.01)
*A61B 5/00* (2006.01)

(58) Field of Classification Search
CPC ..... A43B 7/1455; A61B 5/1038; A61B 5/112; A61B 5/6807; G08B 6/00; G08B 21/18
See application file for complete search history.

(56) References Cited

U.S. PATENT DOCUMENTS

| | | | | |
|---|---|---|---|---|
| 8,974,402 | B2* | 3/2015 | Oddsson | A61B 5/1121 600/595 |
| 10,595,749 | B1* | 3/2020 | Javitt | A61B 5/7455 |
| 2005/0097970 | A1* | 5/2005 | Nurse | A63B 69/0024 73/862.041 |
| 2007/0203435 | A1* | 8/2007 | Novak | A43B 17/00 601/46 |
| 2011/0251520 | A1* | 10/2011 | Shieh | A43D 1/02 600/587 |
| 2016/0206499 | A1* | 7/2016 | Shim | A61F 2/70 |
| 2017/0112712 | A1* | 4/2017 | Chawan | A61H 23/02 |
| 2017/0116869 | A1* | 4/2017 | Pape | G09B 5/02 |
| 2017/0340058 | A1* | 11/2017 | Madore | A43B 7/1435 |
| 2018/0055415 | A1* | 3/2018 | Nakao | A61B 5/224 |
| 2019/0209071 | A1 | 7/2019 | Oddsson et al. | |
| 2020/0000373 | A1* | 1/2020 | Agrawal | A61B 5/7267 |
| 2020/0060378 | A1* | 2/2020 | Roh | A43B 3/34 |
| 2020/0060379 | A1* | 2/2020 | Roh | A61B 5/486 |
| 2020/0061946 | A1* | 2/2020 | Roh | B29D 35/122 |
| 2020/0093400 | A1* | 3/2020 | Hamner | A61N 1/0484 |

FOREIGN PATENT DOCUMENTS

| | | |
|---|---|---|
| KR | 10-1724869 B1 | 4/2017 |
| KR | 20190012986 A | 2/2019 |
| WO | WO-2012/112931 A2 | 8/2012 |

OTHER PUBLICATIONS

Extended European Search Report dated Jan. 29, 2021 for Application No. EP 20 19 8153.

Roll, R. et al., "Cutaneous afferents from human plantar sole contribute to body posture awareness" *NeuroReport*, vol. 13, No. 15, Oct. 2002, pp. 1957-1961.

* cited by examiner

SMART INSOLE AND BALANCE ENHANCEMENT DEVICE COMPRISING THE SAME

CROSS-REFERENCE TO RELATED APPLICATION

This application claims priority under 35 U.S.C. § 119 to Korean Patent Application No. 10-2019-0118121 filed on Sep. 25, 2019, in the Korean Intellectual Property Office, the entire contents of which are incorporated herein by reference in their entirety.

BACKGROUND

1. Field

Some example embodiments relate to a smart insole and/or a balance enhancement device including the smart insole.

2. Description of the Related Art

A user wears shoes in daily life to protect feet of the user comfortably and safely. In recent years, wearable devices are developed to detect a gait pattern of the user and to assist the user to stably walk by providing a sensor and/or an actuator to a shoe.

SUMMARY

Some example embodiments relate to a smart insole configured to be worn by a user.

In some example embodiments, the smart insole may include a support layer; a plurality of pressure sensors associated with the support layer, the plurality of pressure sensors configured to sense a pressure applied thereto by a foot of the user; a plurality of vibrators associated with the support layer, the plurality of vibrators configured to generate a vibration; and a controller configured to, determine a center of pressure (COP) of the foot of the user based on the pressure sensed by each of the plurality of pressure sensors, and control the plurality of vibrators based on a positional relationship between a setting point and the COP.

In some example embodiments, the plurality of vibrators is configured to generate the vibration such that an intensity of the vibration is less than a threshold of a sole of the foot of the user.

In some example embodiments, the controller is configured to control the plurality of vibrators based on information on at least one of a distance from the COP to the setting point and a direction from the COP toward the setting point.

In some example embodiments, the controller is configured to control the plurality of vibrators such that, among the plurality of vibrators, an intensity of the vibration rearward of the setting point is greater than that of an intensity of the vibration provided forward of the setting point, in response to the controller determining that the COP is in front of the setting point.

In some example embodiments, the controller is configured to control the plurality of vibrators such that ones of the plurality of vibrators rearward of the setting point vibrate and ones of the plurality of vibrators forward of the setting point do not vibrate, in response to the controller determining that the COP is in front of the setting point.

In some example embodiments, the controller is configured to, determine whether a distance from a first auxiliary line to the COP is greater than or equal to a first threshold distance, the first auxiliary line being perpendicular to a longitudinal direction of the support layer and intersecting the setting point, and determine that the COP is positioned at the front of the setting point, if the distance from the first auxiliary line to the COP is greater than or equal to the first threshold distance and the COP is positioned at the front of the setting point.

In some example embodiments, the controller is configured to control the plurality of vibrators such that, among the plurality of vibrators, an intensity of the vibration on a right side of the setting point is greater than an intensity of the vibration on a left side of the setting point, in response to the controller determining that the COP is on the left side of the setting point.

In some example embodiments, the controller is configured to control the plurality of vibrators such that ones of the plurality of vibrators on the right side of the setting point vibrate and ones of the plurality of vibrators on the left side of the setting point do not vibrate, in response to the controller determining that the COP is on the left side of the setting point.

In some example embodiments, the controller is configured to, determine whether a distance from a second auxiliary line is greater than or equal to a second setting threshold, the second auxiliary line being parallel to a longitudinal direction of the support layer and intersecting the setting point to the COP, and determine that the COP is positioned on the left side of the setting point, if the distance from the second auxiliary line is greater than or equal to the second setting threshold and the COP is positioned at the left of the setting point.

In some example embodiments, the plurality of vibrators include a front vibrator configured to apply a vibration to a forefoot of the user; and a rear vibrator configured to apply a vibration to a rearfoot of the user.

In some example embodiments, the controller is configured to vibrate one or more of the front vibrator and the rear vibrator based on the positional relationship between the setting point and the COP.

In some example embodiments, the front vibrator includes a right front vibrator and a left front vibrator that are aligned in a width direction of the support layer, and wherein the controller is configured to control plurality of vibrators such that the right front vibrator vibrates and the left front vibrator does not vibrate, in response to the controller determining that the COP is positioned on a left side of the setting point.

In some example embodiments, the smart insole further includes a base configured to support the support layer; and a cover detachably provided to the base, wherein the support layer is provided between the base and the cover.

Some example embodiments relate to a smart insole configured to be worn by a user.

In some example embodiments, the smart insole includes a support layer; a plurality of pressure sensors associated with the support layer, the plurality of pressure sensors configured to sense a pressure applied thereto by a foot of the user; a plurality of vibrators associated with the support layer, the plurality of vibrators configured to generate a vibration having an intensity less than a threshold of a sole of the foot of the user; and a controller configured to, determine a center of pressure (COP) of the foot of the user based on the pressure sensed by each of the plurality of pressure sensors, determine whether the user is in an abnormal condition of balance based on a positional relationship between a setting point and the COP, and control the plurality of vibrators such that the intensity of the vibration is different in at least a portion of the plurality of vibrators.

In some example embodiments, the controller is configured to, determine that the user is in the abnormal condition of balance in response to the controller determining that the COP is in front of or behind the setting point, and control the plurality of vibrators such that, among the plurality of vibrators, the intensity of the vibration forward of the setting point differs from the intensity of the vibration rearward of the setting point, in response to the controller determining that the COP is in front of or behind the setting point.

In some example embodiments, the controller is configured to, determine that the user is in the abnormal condition of balance in response to the controller determining that the COP is on a left side or on a right side of the setting point, and control the plurality of vibrators such that, among the plurality of vibrators, the intensity of the vibration on the left side of the setting point differs from the intensity of the vibration on the right side of the setting point in response to the controller determining that the COP is on the left side or on the right side of the setting point.

Some example embodiments relate to a balance enhancement device.

In some example embodiments, the balance enhancement device may include a left smart insole including a left support layer configured to support a left foot of a user, the left support layer having at least one left pressure sensor and at least one left vibrator associated therewith; a right smart insole including a right support layer configured to support a right foot of the user, the right support layer having at least one right pressure sensor and at least one right vibrator associated therewith; and a controller configured to control the at least one left vibrator and the at least one right vibrator such that an intensity of a vibration generated thereby differs based on a pressure value measured by the left pressure sensor and the right pressure sensor.

In some example embodiments, the controller is configured to control the at least one left vibrator and the at least one right vibrator such that the intensity of the vibration of the at least one right vibrator is greater the intensity of the vibration of the at least one left vibrator, in response to the controller determining that the pressure value measured by the at least one left pressure sensor is greater than the pressure value measured by the at least one right pressure sensor.

In some example embodiments, the controller is configured to control the at least one left vibrator and the at least one right vibrator such that the at least one right vibrator vibrates and the left at least one vibrator does not vibrate, in response to the controller determining that the pressure value measured by the left pressure sensor is greater than the pressure value measured by the right pressure sensor.

In some example embodiments, the at least one left vibrator and the at least one right vibrator are configured to generate the vibration such that the intensity of the vibration is less than a threshold of a sole of the user.

Additional aspects of example embodiments will be set forth in part in the description which follows and, in part, will be apparent from the description, or may be learned by practice of the disclosure.

BRIEF DESCRIPTION OF THE DRAWINGS

These and/or other aspects will become apparent and more readily appreciated from the following description of example embodiments, taken in conjunction with the accompanying drawings of which.

DETAILED DESCRIPTION

Figure 1:
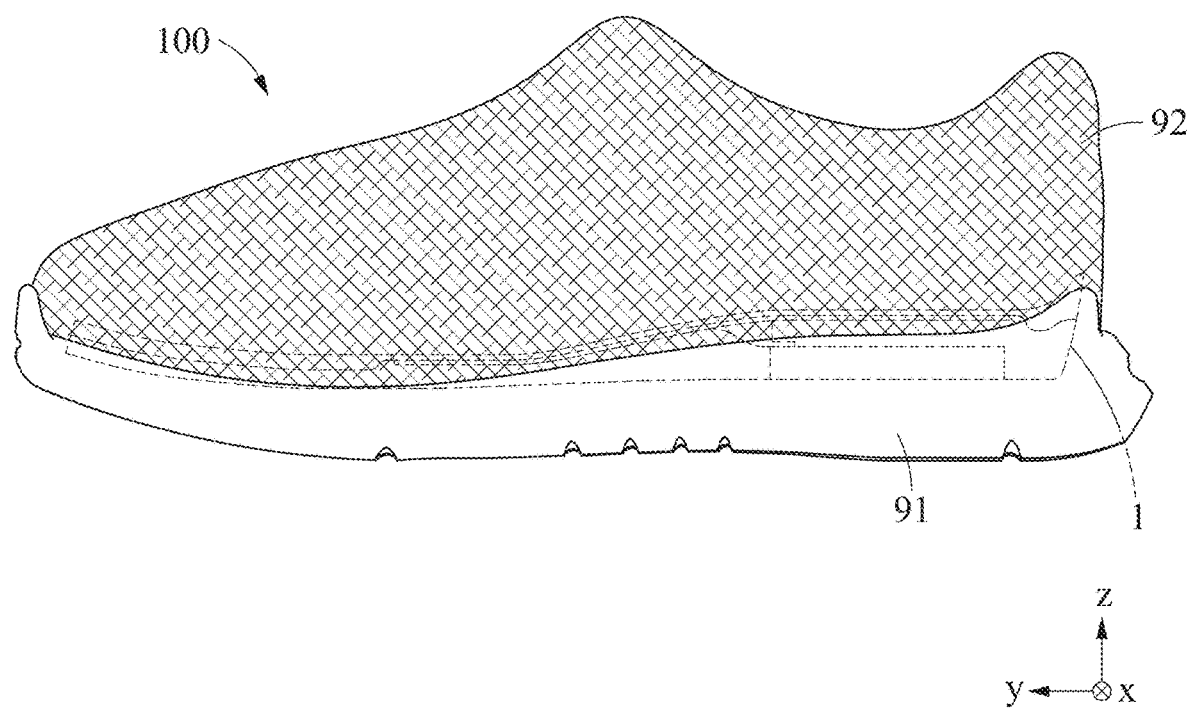
FIG. 1 is a side view of a smart shoe according to at least one example embodiment.

Hereinafter, some example embodiments will be described in detail with reference to the accompanying drawings. Regarding the reference numerals assigned to the elements in the drawings, it should be noted that the same elements will be designated by the same reference numerals, wherever possible, even though they are shown in different drawings. Also, in the description of example embodiments, detailed description of well-known related structures or functions will be omitted when it is deemed that such description will cause ambiguous interpretation of the present disclosure.

In addition, terms such as first, second, A, B, (a), (b), and the like may be used herein to describe components. Each of these terminologies is not used to define an essence, order or sequence of a corresponding component but used merely to distinguish the corresponding component from other component(s). It should be noted that if it is described in the specification that one component is "connected", "coupled", or "joined" to another component, a third component may be "connected", "coupled", and "joined" between the first and second components, although the first component may be directly connected, coupled or joined to the second component.

A component including a common function with a component in one example embodiment is described using the same term in another example embodiment. Unless the context clearly indicates otherwise, description made in one example embodiment may apply to another example embodiment and repetitive description is omitted.

Figure 2:
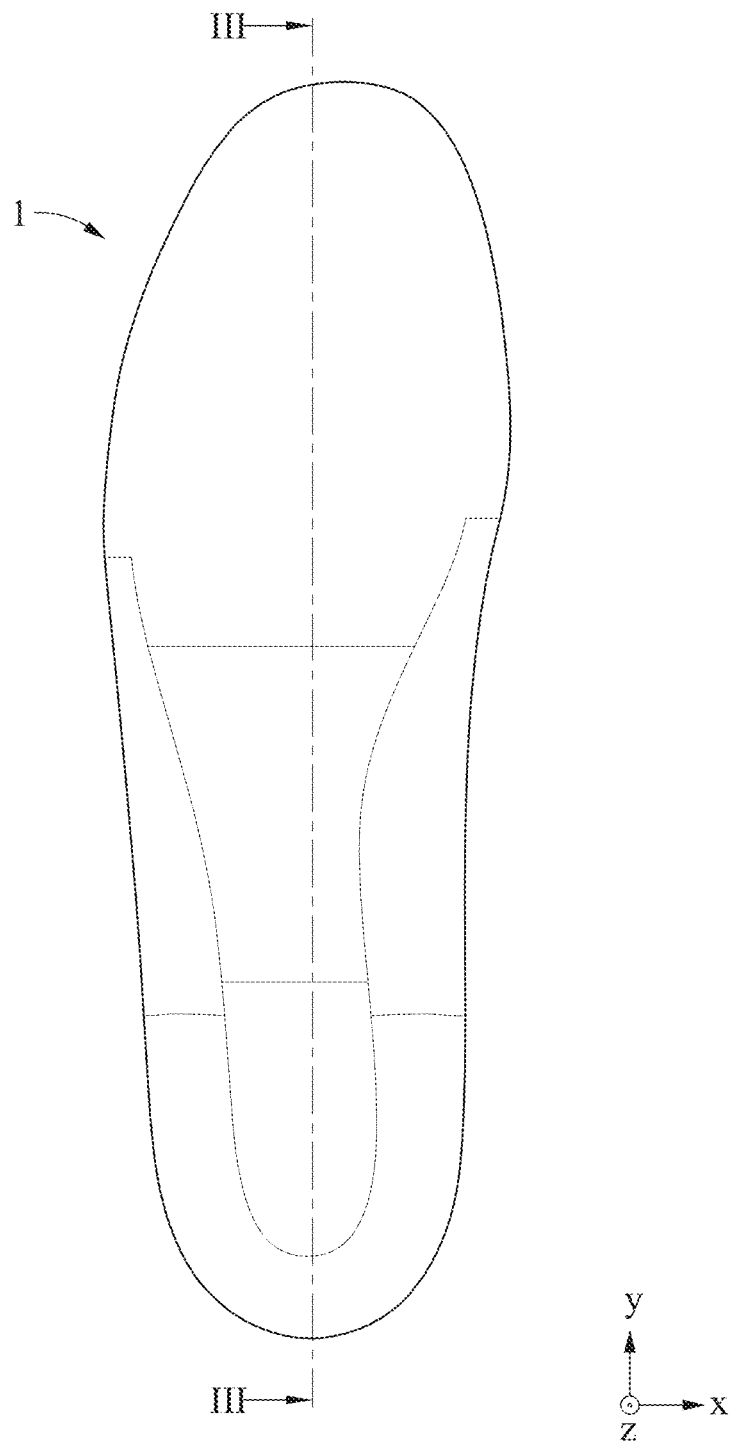
FIG. 2 is a top view illustrating a smart insole according to at least one example embodiment.
Figure 3:
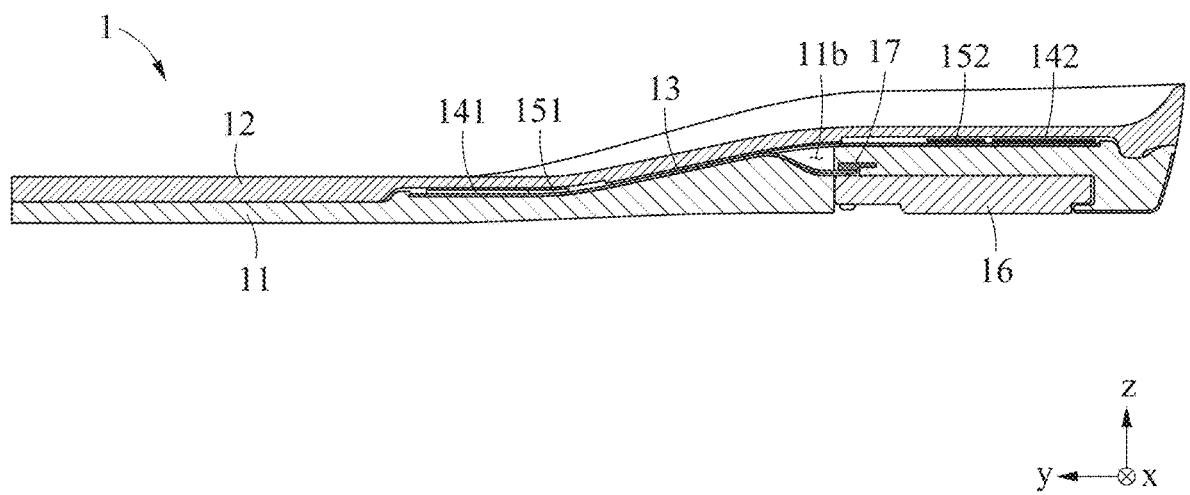
FIG. 3 is a cross-sectional view illustrating the smart insole cut along line of FIG. 2.
Figure 4:
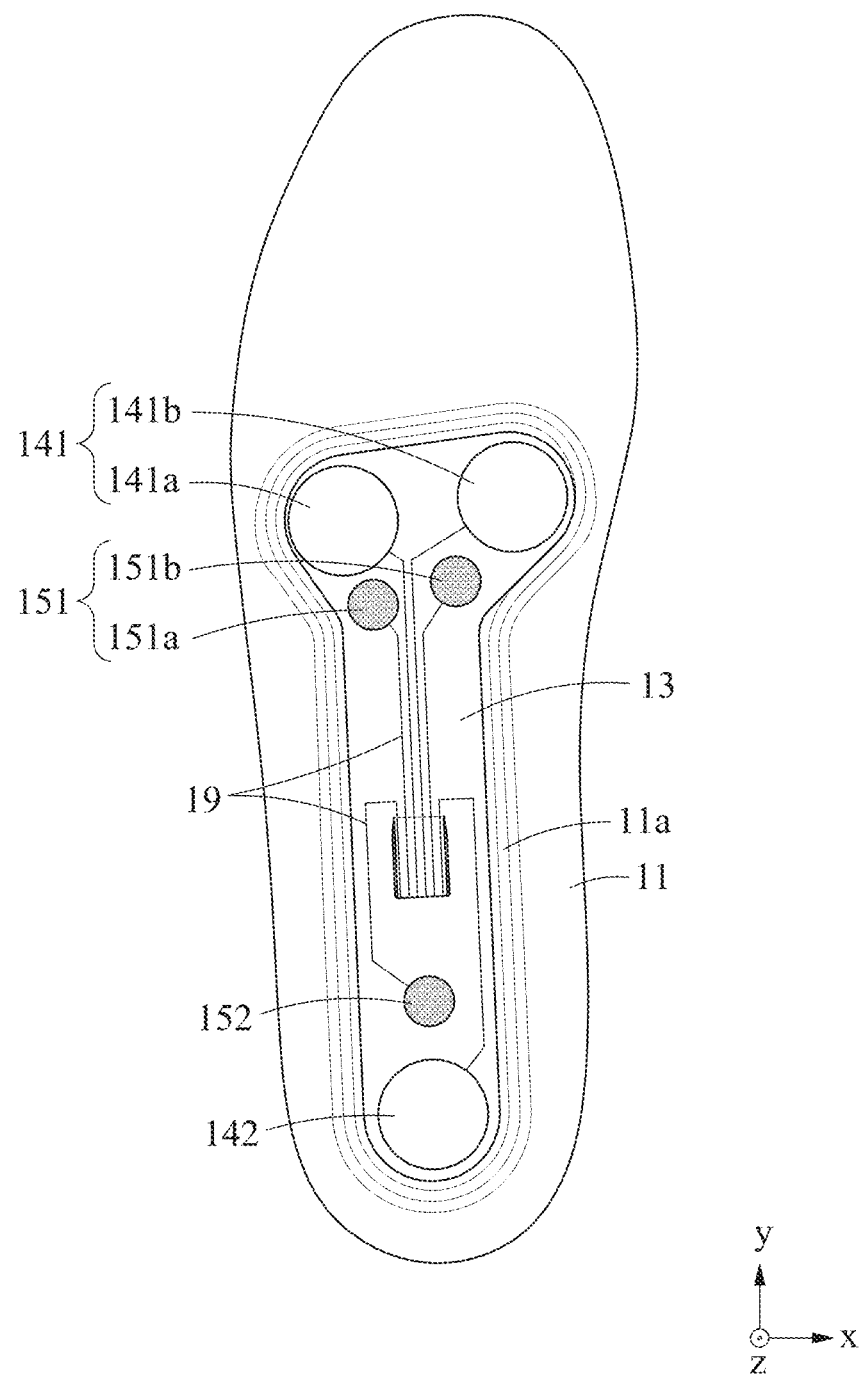
FIG. 4 is a top view illustrating a smart insole from which a cover is separated according to at least one example embodiment.

FIG. 1 is a side view of a smart shoe according to at least one example embodiment, FIG. 2 is a top view illustrating a smart insole according to at least one example embodiment, FIG. 3 is a cross-sectional view illustrating the smart insole cut along line III-III of FIG. 2, and FIG. 4 is a top view illustrating a smart insole from which a cover is separated according to at least one example embodiment.

Referring to FIGS. 1 to 4, a smart shoe 100 may include a smart insole 1, a midsole 91, and an upper 92. The smart shoe 100 may sense pressure applied from a foot of a user using a plurality of pressure sensors 141 and 142 provided to the smart insole 1, and may verify a center of pressure (COP) of a sole of the user. The smart shoe 100 may apply a vibration to the sole of the user using a plurality of vibrators 151 and 152 provided to the smart insole 1. The plurality of vibrators 151 and 152 may apply the vibration to a forefoot and/or rearfoot of the sole of the user.

In the following direction, a longitudinal direction of the smart shoe 100 denotes a y-axial direction, a widthwise direction of the smart shoe 100 denotes an x-axial direction, and a height direction of the smart shoe 100 denotes a z-axial direction. Hereinafter, the term "front" denotes +y direction and the term "rear" denotes -y direction in a coordinate system of FIG. 1, unless the context clearly indicates otherwise.

The smart insole 1 may sense the pressure applied from the sole of the user and may apply an appropriate stimulus to the sole of the user, thereby enhancing balance of the user. For example, if the COP of the sole of the user is too far forward, the smart insole 1 may enhance a sensitivity of the rearfoot of the user by applying a vibration to a rear portion of the sole of the user, that is, the rearfoot of the user to cause the COP of the sole of the user move backward. For example, a stimulus applied by the smart insole 1 to the user may be less than or equal to a threshold.

The smart insole 1 may include a surface in contact with the sole of the user and may support the foot of the user. The smart insole 1, aside from an electronic device, for example, the pressure sensors 141 and 142 and/or the vibrators 151 and 152, provided therein, may be formed of a flexible material to enhance a fitting sense of the user. The smart insole 1 may insert inward into the upper 92 or may separate from the upper 92 through an opening provided in an upper portion of the upper 92. The smart insole 1 may be provided on a floor of the upper 92. If the upper 92 does not include the floor, the smart insole 1 may be provided on a top surface of the midsole 91.

Here, although the smart insole 1 is described as one component of the smart shoe 100, it is provided as an example only. For example, the smart insole 1 may insert into a sock and may perform a pressure measurement and a vibration application, thereby enhancing the balance of the user. As another example, the smart insole 1 may apply to various wearable devices, for example, a motion assist robot.

The smart insole 1 may include a base 11, a cover 12, a support layer 13, the plurality of pressure sensors 141 and 142, the plurality of vibrators 151 and 152, a controller 16, an insert 17, and a connection line 19. The base 11 and the cover 12 may be combined with each other or may be separated from each other. The user may separate the cover 12 and may clean and/or replace the cover 12. Electronic elements provided in the smart insole 1, for example, the plurality of pressure sensors 141 and 142, the plurality of vibrators 151 and 152, and the controller 16 may be provided to the base 11. The cover 12 may not include any of the electronic elements. The cover 12 makes a direct contact with the sole of the user. Therefore, the cover 12 may be relatively easily contaminated compared to the base 11 that makes an indirect contact with the sole of the user. The user may separate and clean only the cover 12. In this manner, the smart shoe 100 may be maintained to be in a hygienically excellent state.

The base 11 may have a shape corresponding to an internal space of the upper 92. For example, the base 11 may insert inward into the upper 92 through the opening provided in the upper portion of the upper 92. The base 11 may include a base protrusion 11a configured to enhance a combining force with the cover 12 and a base hole 11b configured to guide the connection line 19 to the controller 16.

The base protrusion 11a may protrude upward, may insert into the cover 12, and may support the cover 12 such that the cover 12 does not move relative to the base 11. For example, the base protrusion 11a may be fitted to the cover 12. Here, the expression "fit" may inclusively indicate tight fit and any mutual coupling methods capable of reducing a phenomenon that the cover 12 slides relative to the base 11. The cover 12 may include a groove (not shown) recessed from a bottom surface of the cover 12, and the base protrusion 11a may insert into the groove. The base protrusion 11a may prevent the cover 12 from sliding in a horizontal direction, for example, the x-axial direction or the y-axial direction. The base protrusion 11a may surround the support layer 13 and may fasten the support layer 13. Although the base protrusion 11a is illustrated in a shape of a closed curve, it is provided as an example only. For example, the base protrusion 11a may be in a shape including a plurality of unit bodies.

The base hole 11b may be formed to vertically penetrate the base 11. The base hole 11b may be formed in a direction perpendicular to the smart insole 1, that is, the z-axial direction. The base hole 11b may function as a path that guides the connection line 19 from the top surface to the bottom surface of the base 11. The connection line 19 that passes through the base hole 11b may be connected to the controller 16. According to the above structure, the plurality of pressure sensors 141 and 142 and the plurality of vibrators 151 and 152 may be provided to be close to the foot of the user and the effect from the pressure applied from the foot of the user against the controller 16 may decrease, thereby enhancing the durability of the controller 16.

The base hole 11b may be formed in a space in which the plurality of pressure sensors 141 and 142 and the plurality of vibrators 151 and 152 are absent. That is, the base hole 11b may be formed in a portion that overlaps a midfoot. According to the above structure, during walking of the user, the pressure that applies to the base hole 11b and the connection line 19 passing the base hole 11b may relatively decrease and a disconnection risk of the connection line 19 may also decrease accordingly. For example, during a push-off phase, a relatively strong pressure may apply to a portion that overlaps a forefoot, that is, the pressure sensor 141 and the vibrator 151 provided in a front portion of the smart insole 1. Likewise, during a heel-strike phase, a relatively strong pressure may apply to a portion that overlaps a rearfoot, that is, the pressure sensor 142 and the vibrator 152 provided in a rear portion of the smart insole 1. Meanwhile, during the overall gait phase, a relatively small pressure may apply to a portion that overlaps a middle portion of the smart insole 1, that is, around the base hole 11*b*.

The cover 12 is detachably provided to the base 11. The cover 12 may cover the plurality of pressure sensors 141 and 142 and the plurality of vibrators 151 and 152 to prevent the plurality of pressure sensors 141 and 142 and the plurality of vibrators 151 and 152 from making a direct contact with the foot of the user. A shape of the cover 12 may be approximately similar to a shape of the base 11. The cover 12 may mostly overlap the base 11 based on a vertical direction of the smart insole 1. For example, an electronic part may not be provided in the cover 12. According to the above structure, the user may separate and thereby clean or replace the cover 12 alone. Also, without modifying a structure of the base 11 including various types of electronic elements, the cover 12 in a shape customized for a shape of the foot of the user may be provided. Accordingly, cost and effort used to manufacture the smart shoe 100 may be saved.

The support layer 13 may support the plurality of pressure sensors 141 and 142 and the plurality of vibrators 151 and 152, and may insert inward into the base protrusion 11*a*. The support layer 13 may be fitted to the base protrusion 11*a*. The support layer 13 may be tightly fastened inside the base protrusion 11*a*. The support layer 13 may be formed of a flexible film.

The plurality of pressure sensors 141 and 142 may sense the pressure applied from the sole of the user. The plurality of pressure sensors 141 and 142 may be a pressure sensor, such as, for example, a piezo pressure sensor and a force sensitive resistor (FSR) pressure sensor. Information measured by such a pressure sensor may be used to analyze a gait posture of the user.

The plurality of pressure sensors 141 and 142 may include a front pressure sensor 141 and a rear pressure sensor 142. The front pressure sensor 141 may overlap the forefoot of the user. The rear pressure sensor 142 may overlap the rearfoot of the user. The front pressure sensor 141 may include a first front pressure sensor 141*a* provided on the left and a second front pressure sensor 141*b* provided on the right.

The plurality of vibrators 151 and 152 may generate a vibration and may apply a stimulus to the sole of the user. The plurality of vibrators 151 and 152 may be a vibrator, such as, for example, an eccentric motor. The plurality of vibrators 151 and 152 may generate a vibration with intensity less than a threshold of the sole of the user. The plurality of vibrators 151 and 152 may cause a stochastic resonance on the sole of the user. The stochastic resonance indicates a phenomenon in which, for example, a sensory organ having a set threshold value receives white noise with less than or equal to the threshold value, a sensitivity of the sensory organ improved. In this case, an actual tactile signal transferred to the sole of the user is amplified by resonance with vibration noise, which may make a sense of the sole of the user sensitive.

The plurality of vibrators 151 and 152 may include a front vibrator 151 and a rear vibrator 152. The front vibrator 151 may overlap the forefoot of the user. The rear vibrator 152 may overlap the rearfoot of the user. The front vibrator 151 may include a first front vibrator 151*a* provided on the left and a second front vibrator 151*b* provided on the right.

The controller 16 may include processing circuitry including, but is not limited to, a central processing unit (CPU), an arithmetic logic unit (ALU), a digital signal processor, a microcomputer, a field programmable gate array (FPGA), a programmable logic unit, a microprocessor, application-specific integrated circuit (ASIC), etc. The processing circuitry may execute instructions that configure the processing circuitry as special purpose processing circuitry that determines the COP sensed by the plurality of pressure sensors 141 and 142, and controls the plurality of plurality of vibrators 151 and 152 based on a positional relationship between a setting point and the COP. Therefore, the processing circuitry may improve the functioning of the smart shoe 1 itself by applying an appropriate stimulus to the sole of the user, thereby enhancing balance of the user.

The controller 16 may physically and/or electrically connect to the plurality of pressure sensors 141 and 142 and the plurality of vibrators 151 and 152. The controller 16 may set (or, alternatively, preset) the setting point. Here, the setting point may be an ideal COP. The controller 16 may set, as the setting point, the ideal COP, that is, the COP when the use is standing or walking in a correct posture. The ideal COP may be determined through an empirical study. For example, an empirical study may be performed where users walk on a capacitive pressure platform at their normal pace and the pressure distribution of the users is analyzed to determine the ideal COP, where the ideal COP for different users may be broken up based on age, sex, weight and other factors. The controller 16 may determine the COP, that is, the actual COP based on the pressure sensed by the plurality of pressure sensors 141 and 142.

The controller 16 may control the plurality of vibrators 151 and 152 based on the positional relationship between the setting point and the COP. The controller 16 may control the plurality of vibrators 151 and 152 based on information on at least one of a distance from the COP to the setting point and a direction from the COP toward the setting point.

When the COP is positioned forward of the setting point, the controller 16 may selectively drive a vibrator provided at the rear and may not drive a vibrator provided at the front. In this case, sensitivity of a rearfoot portion of the user increases and a center of gravity of the user moves backward. Accordingly, the COP approaches the setting point. In this manner, the controller 16 may perform a control for enhancing balance of the user.

Likewise, when the COP is positioned rearward of the setting point, the controller 16 may selectively drive a vibrator provided at the front and may not drive a vibrator provided at the rear. In this case, sensitivity of a forefoot portion of the user increases and a center of gravity of the user moves forward. Accordingly, the COP approaches the setting point.

In some example embodiments, the controller 16 may control the selected vibrator to generate the desired intensity of vibration where the vibration has a frequency that changes (e.g. randomly) such that at least a portion of the vibration resonates along with an external stimulus.

In some example embodiments, the controller 16 may estimate a posture of the user by measuring foot pressure of the user, and selectively activate the selected vibrator only when the posture of the user is a walking posture and/or a standing posture. Therefore, the controller 16 may improve the functioning of the smart shoe 1 itself by reducing power consumption of the battery and/or increasing comfortableness that may be experienced by the user.

In some example embodiments, the controller 16 may be in communication with a walking assistance apparatus worn by the user, and instruct the walking assistance apparatus to output an assistance force that re-balances pressures applied to the sole of the user based on the detected COP. walking assistance apparatus 100 may output an assistance force that re-balances pressures applied to the left portion and the right portion of the sole of the user.

The controller 16 may be provided to the smart insole 1. However, it is provided as an example only. For example, the controller 16 may be provided to the midsole 91.

The insert 17 may be provided in the base 11 and may be formed of a more robust material than that of the base 11. For example, the insert 17 may be integrally formed inside the base 11 by forming the base 11 through a resin foaming process and the like in a state in which the base 11 is provided in advance in a frame. The insert 17 may overlap the controller 16 based on a direction perpendicular to the smart insole 1. Although the insert 17 is illustrated to fasten a front end of the controller 16, it is provided as an example only. A plurality of inserts 17 may be provided to fasten another portion of the controller 16. Also, the insert 17 may be in a different shape to fasten a plurality of portions of the controller 16.

The connection line 19 may electrically connect the plurality of pressure sensors 141 and 142 and the plurality of vibrators 151 and 152 to the controller 16. The connection line 19 may extend from the plurality of pressure sensors 141 and 142 and the plurality of vibrators 151 and 152, and may penetrate the base 11. The connection line 19 may extend from the top surface of the base 11 to the bottom surface of the base 11 by penetrating the base hole 11b. An end of the connection line 19 may connect to the controller 16 provided in a lower portion of the base 11. One end of the connection line 19 may be connected to the plurality of pressure sensors 141 and 142 or the plurality of vibrators 151 and 152 and another end of the connection line 19 may be connected to the controller 16. The plurality of pressure sensors 141 and 142 and the plurality of vibrators 151 and 152 may access the controller 16 through the connection line 19. For example, the connection line 19 may be provided on a top surface or a bottom surface of the support layer 13, or may be embedded in the support layer 13. Meanwhile, the connection line 19 may be directly provided to a base 11 without using the support layer 13.

Figure 5:
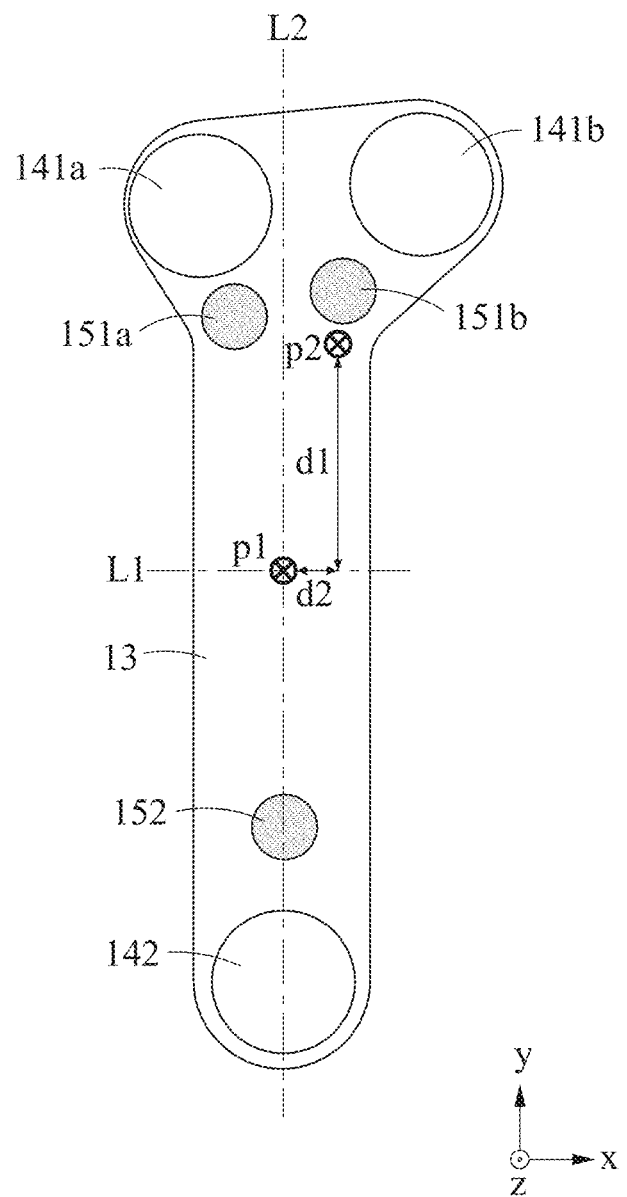
FIG. 5 is a top view illustrating a support layer, a plurality of pressure sensors, and a plurality of vibrators according to at least one example embodiment.
Figure 6:
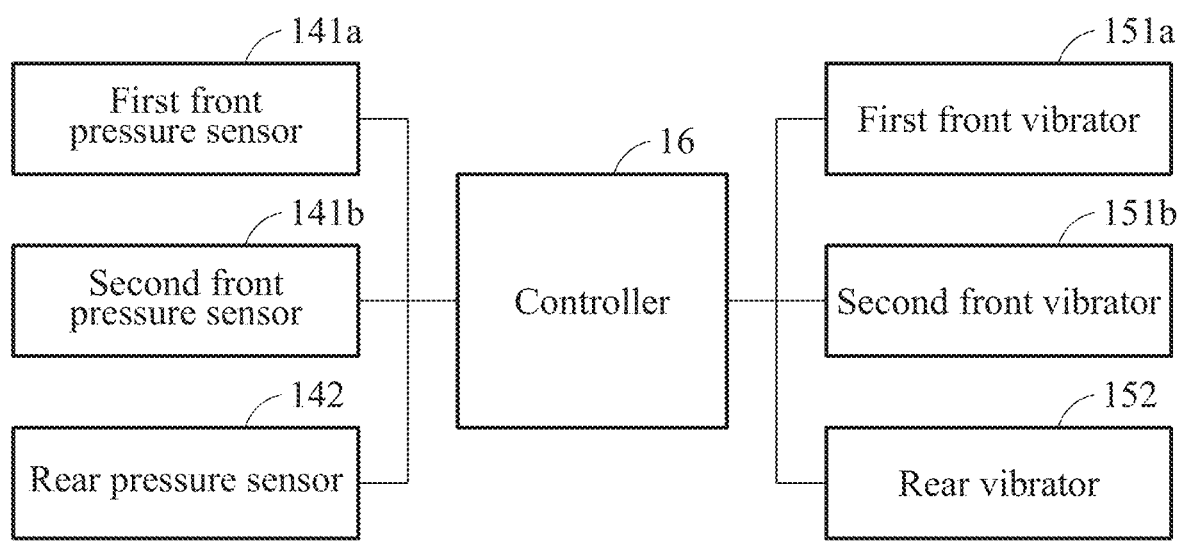
FIG. 6 is a block diagram illustrating a configuration of a smart shoe according to at least one example embodiment.

FIG. 5 is a top view illustrating a support layer, a plurality of pressure sensors, and a plurality of vibrators according to at least one example embodiment, and FIG. 6 is a block diagram illustrating a configuration of a smart shoe according to at least one example embodiment. For clarity of description, a connection line is omitted in FIG. 5.

Referring to FIGS. 5 and 6, the controller 16 may receive pressure information from the first front pressure sensor 141a, the second front pressure sensor 141b, and the rear pressure sensor 142, and may determine a COP p2. The first front pressure sensor 141a may be spaced apart to the left from the second front pressure sensor 141b.

The controller 16 may compare the COP p2 to a setting point p1. For example, the setting point p1 may be an ideal COP point when the user is in a correct posture. The setting point p1 may be set (or, alternatively, preset) and a position of the setting point p1 may vary in real time during use. When the posture of the user leans forward, the COP p2 may be positioned forward of the setting point p1. Likewise, when the posture of the user leans backward, the COP p2 may be positioned rearward of the setting point p1.

For example, referring to FIG. 5, the COP p2 may be positioned at the front and on the right relative to the setting point p1. A distance from a first auxiliary line L1 that is perpendicular to a longitudinal direction (y-axial direction) of the support layer 13 and passes the setting point p1 to the COP p2 may be d1. A distance from a second auxiliary line L2 that is parallel to the longitudinal direction (y-axial direction) of the support layer 13 and passes the setting point p1 to the COP p2 may be d2.

The controller 16 may compare d1 to a first setting distance to generate a comparison result, and may determine whether the COP p2 is positioned at the front of the setting point p1 based on the comparison result. The user may adjust the first setting distance. For example, if the user desires to maintain a relatively high level of balance, the user may set the first setting distance to be relatively small.

If d1 is maintained to be greater than or equal to the first setting distance during a first setting time or more, the controller 16 may determine that the user is in an abnormal condition of balance. The user may adjust the first setting time. For example, if the user desires to maintain a relatively high level of balance, the user may set the first setting time to be relatively short.

Hereinafter, a positional relationship between the setting point p1 and the COP according to an abnormal condition of balance of the user is described with reference to FIGS. 7 to 12.

Figure 7:
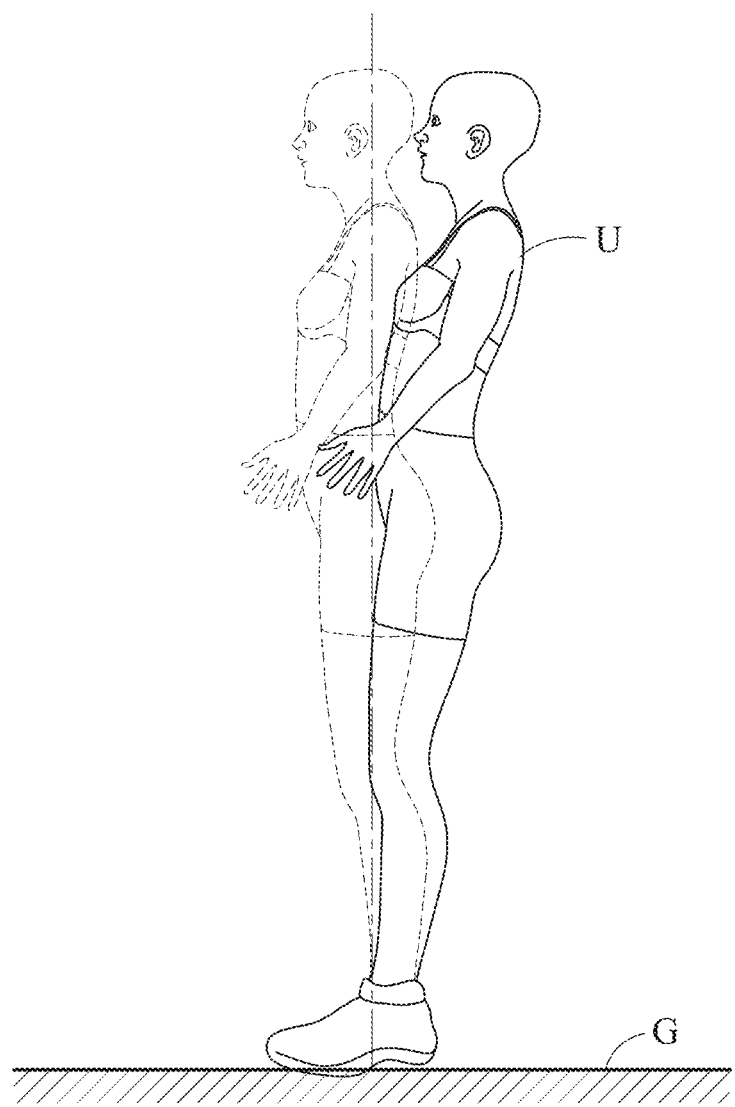
FIG. 7 is a side view illustrating a user of which a posture is biased backward according to at least one example embodiment.
Figure 8:
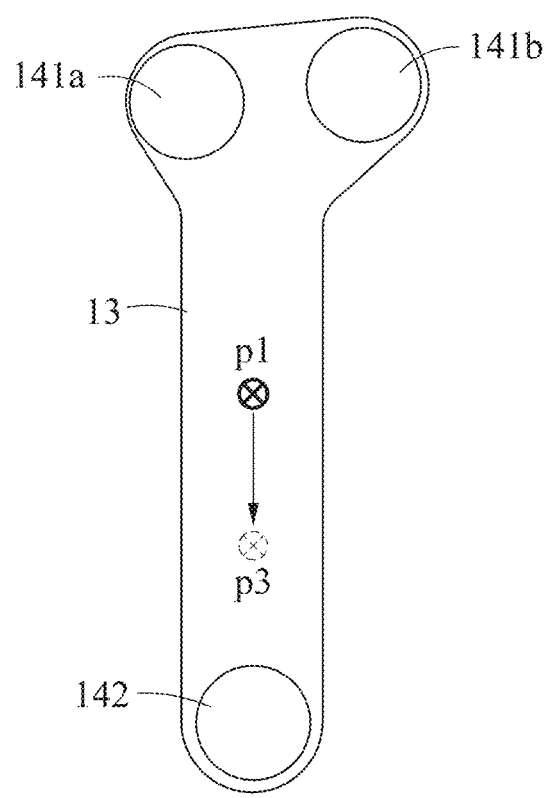
FIG. 8 is a top view illustrating a relationship between a setting point and a center of pressure (COP) in a state of FIG. 7.

FIG. 7 is a side view illustrating a user of which a posture is biased backward, that is, leans backward according to at least one example embodiment, and FIG. 8 is a top view illustrating a relationship between a setting point and a COP in a state of FIG. 7.

Referring to FIGS. 7 and 8, when a posture of a user U leans backward based on a ground G, for example, when an upper body of the user U leans backward, a COP p3 determined by the plurality of pressure sensors 141a, 141b, and 142 may be positioned at the rear of the setting point p1. For example, a magnitude of pressure measured by the rear pressure sensor 142 may be greater than that of pressure measured by the first front pressure sensor 141a and/or second front pressure sensor 141b.

In this case, the controller 16 (FIG. 6) may control an intensity of vibration of a vibrator provided in a front portion to be greater than that of a vibrator provided in a rear portion, thereby enhancing a sensitivity of a forefoot of the user U. For example, the controller 16 may drive only the vibrator provided in the front portion and may not drive the vibrator provided in the rear portion.

Figure 9:
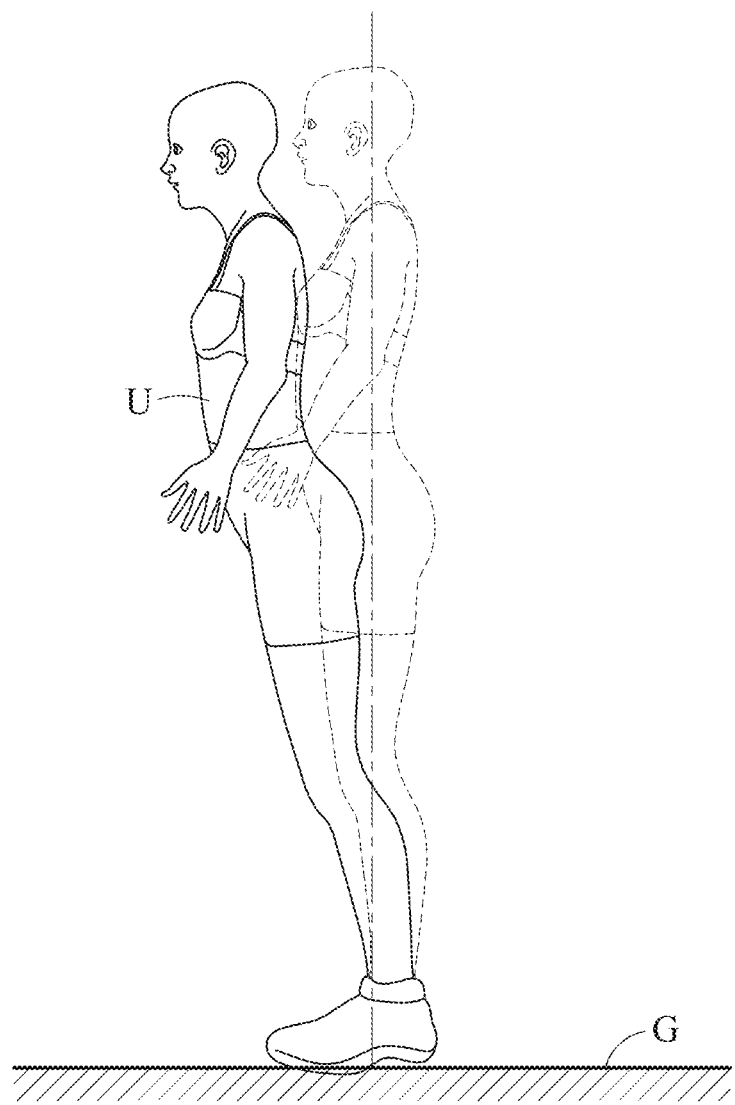
FIG. 9 is a side view illustrating a user of which a posture is biased forward according to at least one example embodiment.
Figure 10:
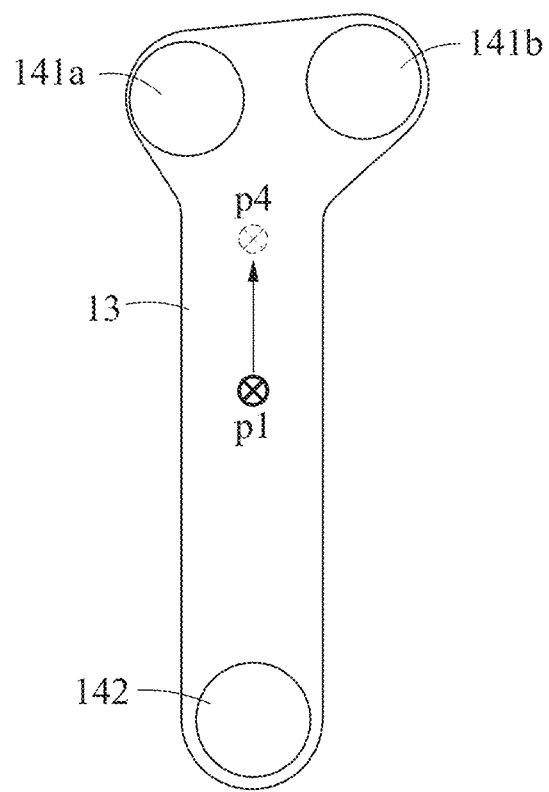
FIG. 10 is a top view illustrating a relationship between a setting point and a COP in a state of FIG. 9.

FIG. 9 is a side view illustrating a user of which a posture is biased forward, that is, leans forward according to at least one example embodiment, and FIG. 10 is a top view illustrating a relationship between a setting point and a COP according to at least one example embodiment.

Referring to FIGS. 9 and 10, when a posture of a user U leans forward based on a ground G, for example, when an upper portion of the user U leans forward, a COP p4 determined by the plurality of pressure sensors 141a, 141b, and 142 may be positioned at the front of the setting point p1. For example, a magnitude of pressure measured by the first front pressure sensor 141a and/or the second front pressure sensor 141b may be greater than that of pressure measured by the rear pressure sensor 142.

In this case, the controller 16 may control a magnitude of vibration of a vibrator provided in a rear portion to be greater than that of vibration of a vibrator provided in a front portion, thereby enhancing a sensitivity of a rearfoot of the user U. For example, the controller 16 may drive only the vibrator provided in the rear portion and may not drive the vibrator provided in the front portion.

Figure 11:
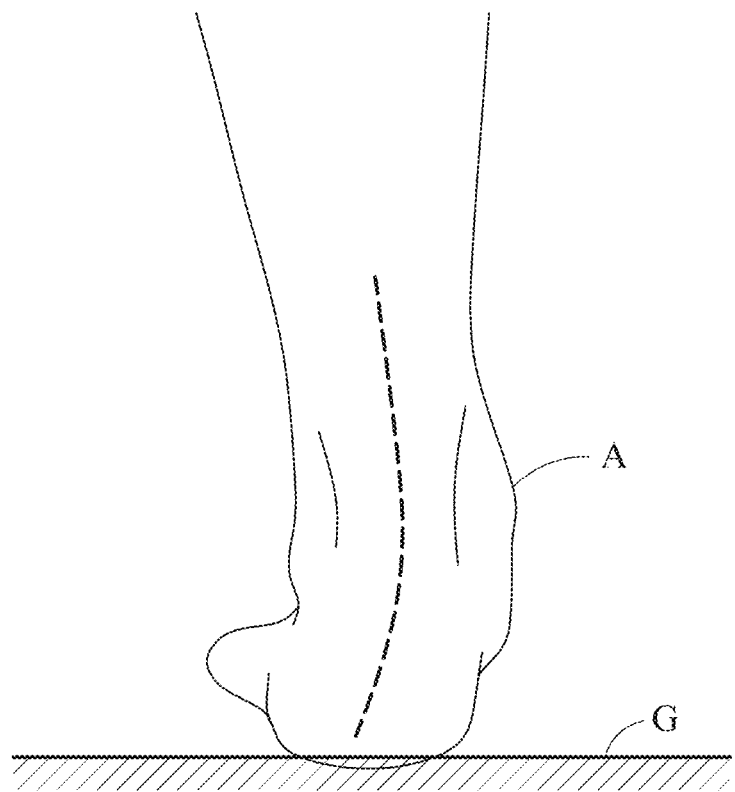
FIG. 11 is a rear view illustrating an off-balance state of an ankle.
Figure 12:
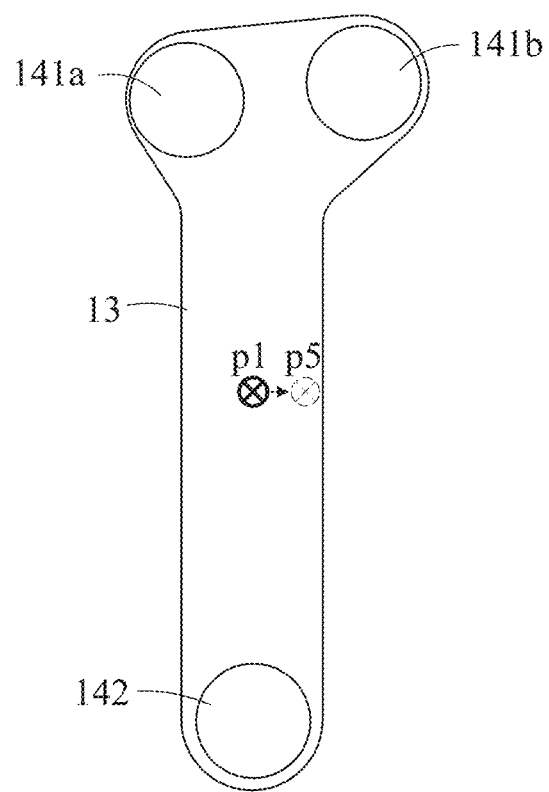
FIG. 12 is a top view illustrating a relationship between a setting point and a COP in a state of FIG. 11.

FIG. 11 is a rear view illustrating an off-balance state of an ankle, and FIG. 12 is a top view illustrating a relationship between a setting point and a COP in a state of FIG. 11.

Referring to FIGS. 11 and 12, when an ankle A of a user bends inward, a relatively large weight of a user may be loaded to inside of a foot. A COP p5 determined by the plurality of pressure sensors 141a, 141b, and 142 may be positioned on the right of a setting point p1. For example, a magnitude of pressure measured by the second front pressure sensor 141b may be greater than that of pressure measured by the first front pressure sensor 141a.

In this case, the controller 16 may control an intensity of vibration of a vibrator provided on the left to be greater than that of a vibrator provided on the left, thereby enhancing a sensitivity of a left side of the foot of the user. For example, the controller 16 may drive only the vibrator provided on the left and may not drive the vibrator provided on the right.

Figure 13:
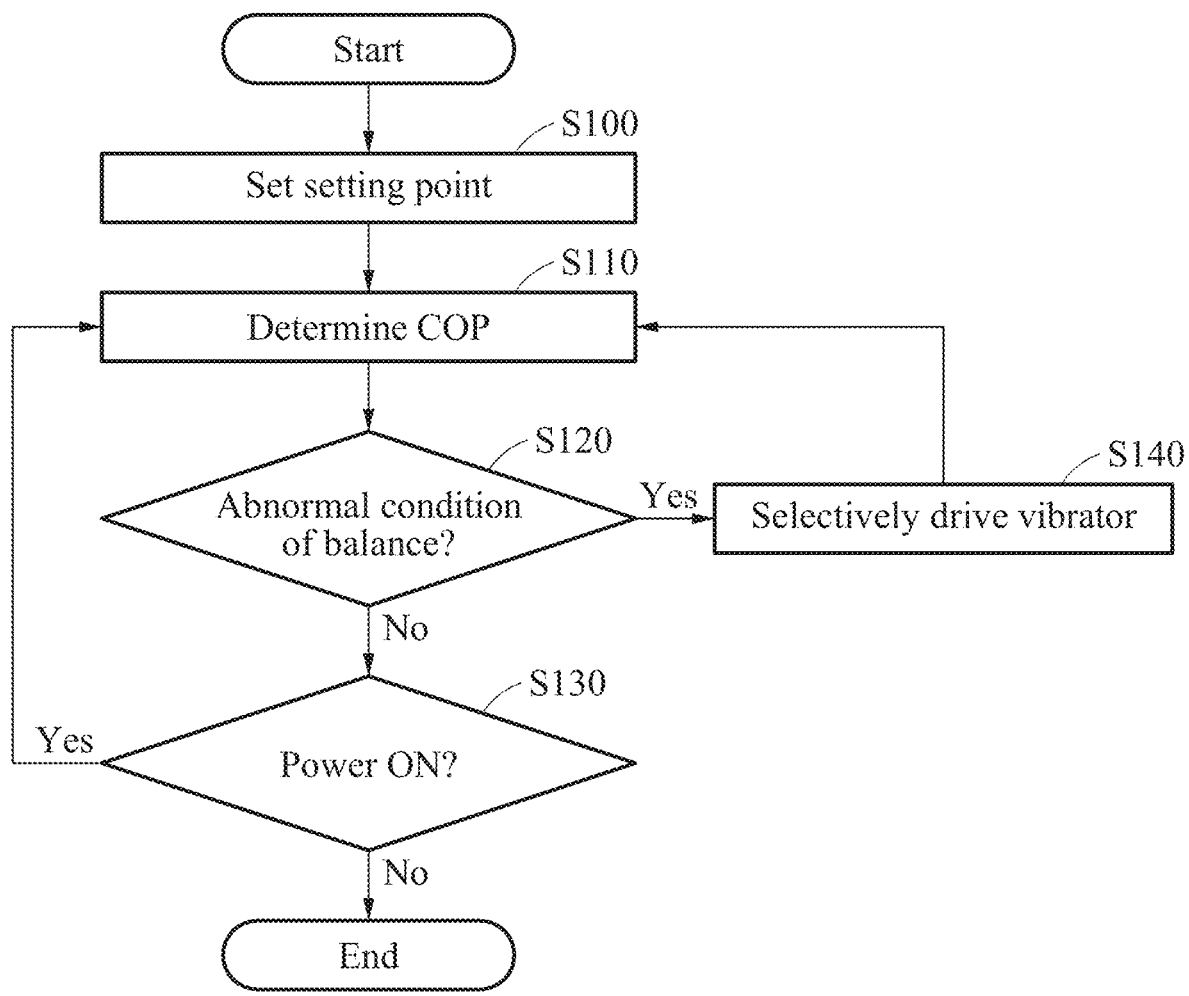
FIG. 13 is a flowchart illustrating sequence in which a smart shoe maintains balance according to at least one example embodiment.
Figure 14:
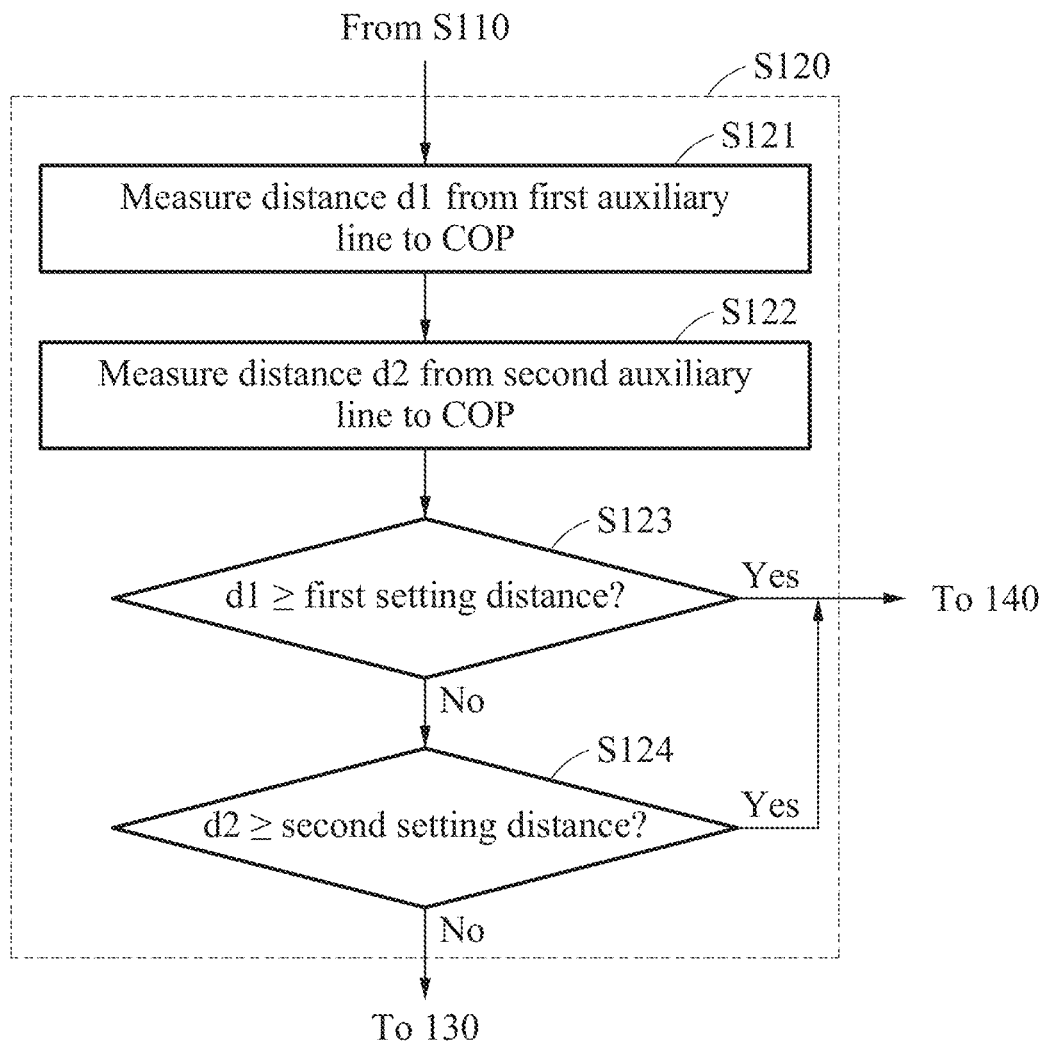
FIG. 14 is a flowchart illustrating an operation of determining whether balance is being maintained of FIG. 13.
Figure 15:
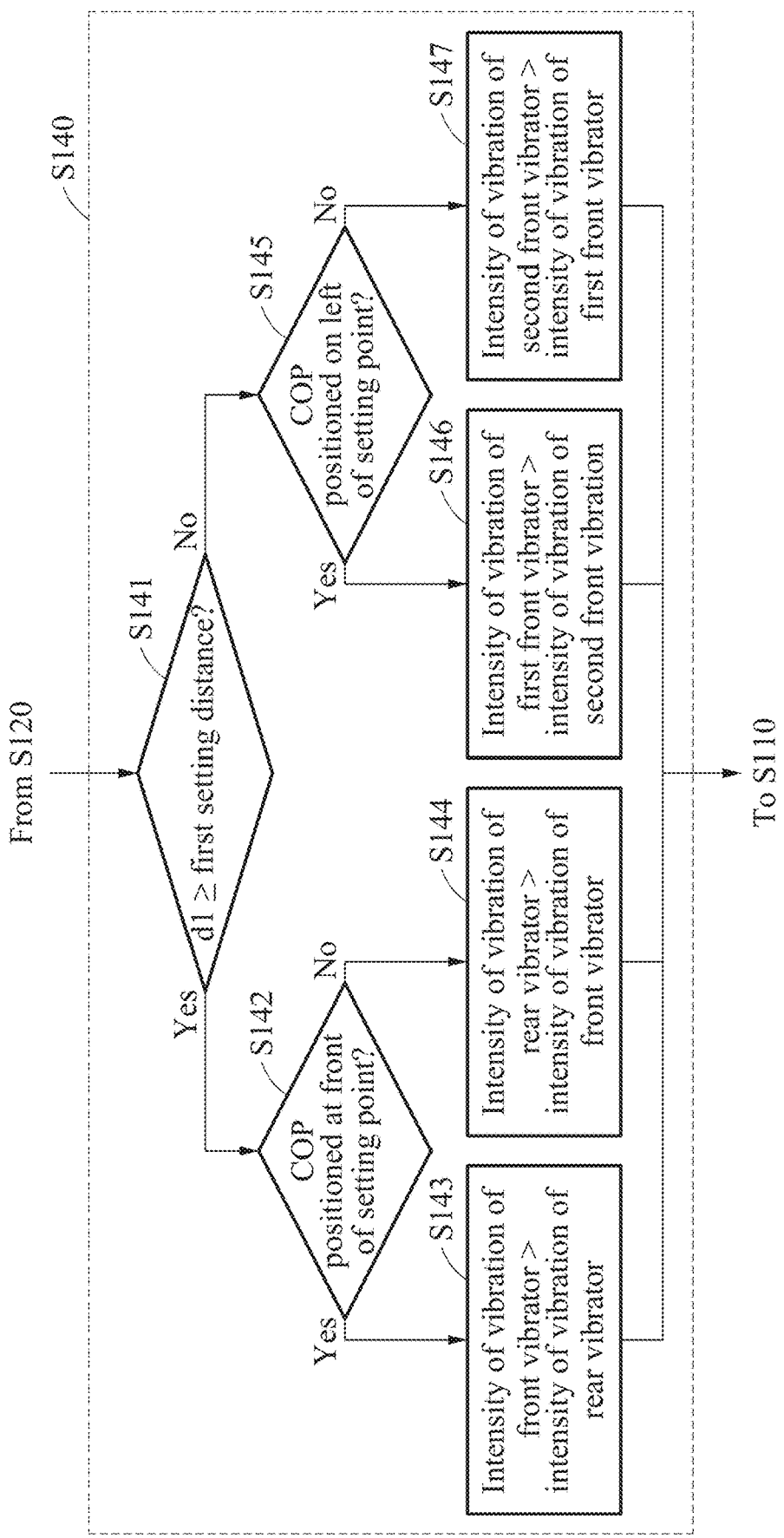
FIG. 15 is a flowchart illustrating an operation of selectively driving a vibrator of FIG. 13.

FIG. 13 is a flowchart illustrating sequence in which a smart shoe maintains balance according to at least one example embodiment, FIG. 14 is a flowchart illustrating an operation of determining whether balance is being maintained of FIG. 13, and FIG. 15 is a flowchart illustrating an operation of selectively driving a vibrator of FIG. 13.

Referring to FIGS. 13 to 15, the smart shoe may enhance balance of a user by selectively controlling a vibration to be applied from a plurality of vibrators. A method of enhancing, by the smart shoe, the balance of the user may include operation S100 of setting a setting point, operation S110 of determining a COP, operation S120 of determining whether the balance is being maintained, operation S130 of verifying whether a power is ON, and operation S140 of selectively driving a vibrator. Operations S100 to S140 may be performed by the controller 16.

In operation S100, the controller 16 may receive an input of setting point data from the user. For example, the user may input the setting point data in advance before performing a balance enhancement operation, or may continuously update a setting point through a wireless communication while performing the balance enhancement operation. The setting point may be set as an ideal COP point in a state in which the user is maintained in a correct posture.

In operation S110, the controller 16 may determine the COP. The controller may determine the COP based on pressure information sensed by the plurality of pressure sensors 141, 142. For example, if a pressure value measured by one or more of the pressure sensors 141 provided at the front of the setting point is greater than a pressure value measured by the pressure sensor 142 provided at the rear of the setting point, the controller 16 may determine the COP to be positioned forward of the setting point.

In operation S120, the controller 16 may determine whether the user is currently in an abnormal condition of balance. The controller 16 may determine whether the user is in the abnormal condition of balance based on a positional relationship between the setting point and the COP. When the COP is positioned forward or rear of the setting point, the controller 16 may determine that the user is in an abnormal condition of front-and-rear balance and may control, among the plurality of vibrators, an intensity of vibration of a vibrator provided at the front of the setting point to differ from that of a vibrator provided at the rear of the setting point.

For example, when the COP is positioned forward of the setting point, the controller 16 may control, among the plurality of vibrators, intensity of vibration of the vibrator 152 provided at the rear of the setting point to be greater than that of the vibrators 151 provided in front of the setting point. In this manner, it is possible to relatively enhance a sensitivity of a rearfoot of the user and to make the COP move backward. Accordingly, the COP may approach the setting point.

For example, when the COP is positioned rearward of the setting point, the controller 16 may control, among the plurality of vibrators, intensity of vibration of one or more of the vibrators 151 at the front of the setting point to be greater than that of the vibrator 152 provided at the rear. In this manner, it is possible to relatively enhance a sensitivity of a forefoot of the user and to make the COP move forward. Accordingly, the COP may approach the setting point.

When the COP is positioned on the left or on the right of the setting point, the controller 16 may determine that the user is in an abnormal condition of left-and-right balance and may control, among the plurality of vibrators, intensity of vibration of the vibrator 141a present on the left of the setting point to differ from that of the vibrator 141b present on the right of the setting point.

For example, when the COP is positioned on the left of the setting point, the controller 16 may control, among the plurality of vibrators, intensity of vibration of the vibrator 141b present on the right of the setting point to be greater than that of the vibrator 141a present on the left of the setting point. In this manner, it is possible to relatively enhance a sensitivity of a right-side portion of a foot of the user and to make the COP move to the right. Accordingly, the COP may approach the setting point.

For example, when the COP is positioned on the right of the setting point, the controller 16 may control, among the plurality of vibrators, intensity of vibration of the vibrator 141a present on the left of the setting point to be greater than that of the vibrator 141b present on the right of the setting point. In this manner, it is possible to relatively enhance a sensitivity of a left-side portion of a foot of the user and to make the COP move to the left. Accordingly, the COP may approach the setting point.

Referring to FIGS. 13 and 14, operation S120 in which the controller 16 determines whether the user is in an abnormal condition of balance may include operation S121 of measuring a distance d1 from a first auxiliary line to the COP, operation S122 of measuring a distance d2 from a second auxiliary line to the COP, operation S123 of determining whether d1 is greater than or equal to a first setting distance, and operation S124 of determining whether d2 is greater than or equal to a second setting distance. Here, referring to FIG. 5, the first auxiliary line refers to an auxiliary line that is perpendicular to a longitudinal direction of a support layer and passes the setting point, and the second auxiliary line refers to an auxiliary line that is parallel to the longitudinal direction of the support layer and passes the setting point.

If the controller 16 determines, in operation S123, that d1 is greater than or equal to the first setting distance and/or determines, in operation S124 that d2 is greater than or equal to the second setting distance, the controller 16 may determine that the user is in an abnormal condition of balance. For example, if d1 is greater than or equal to the first setting distance, the controller 16 may determine that the user is in an abnormal condition of front-and-rear balance. For example, if d2 is greater than or equal to the second setting distance, the controller 16 may determine that the user is in an abnormal condition of left-and-right balance. The first setting distance and/or the second setting distance are adjustable. When the controller 16 determines that the user is in the abnormal condition of balance, the controller 16 may selectively drive one or more of the plurality of vibrators 151, 152.

If the controller 16 determines that the user is not in the abnormal condition of balance (e.g., is normally balanced), in operation S130, the controller 16 may determine whether to iteratively re-perform the determination of the COP based on whether the power is ON. When the power is ON, the controller 16 may perform operation S110 of receiving pressure information from the plurality of pressure sensors and determining the COP. When the power is OFF, the controller 16 may stop a balance enhancement operation.

In contrast, if the controller 16 determines that the user is in the abnormal condition of balance, in operation S140, the controller 16 may selectively drive one or more of the plurality of vibrators 151, 152.

Referring to FIGS. 13 and 15, operation S140 may include operation S141 of determining whether d1 is greater than or equal to the first setting distance, operation S142 of determining whether the COP is positioned at the front of the setting point, operation S143 of controlling intensity of vibration of one or more front vibrators 151 to be greater than that of a rear vibrator 152, operation S144 of controlling intensity of vibration of the rear vibrator 152 to be greater than that of one or more of the front vibrators 151, operation S145 of determining whether the COP is positioned on the left of the setting point, operation S146 of controlling intensity of vibration of a first front vibrator to be greater than that of a second front vibrator, and operation S147 of controlling intensity of vibration of the second front vibrator 151b to be greater than that of the first front vibrator 151a. Here, the first front vibrator 151a and the second front vibrator 151b are spaced apart from each other in a direction that intersects the longitudinal direction of the support layer, and the first front vibrator 151a denotes a vibrator provided on the left of the second front vibrator 151b.

Figure 16:
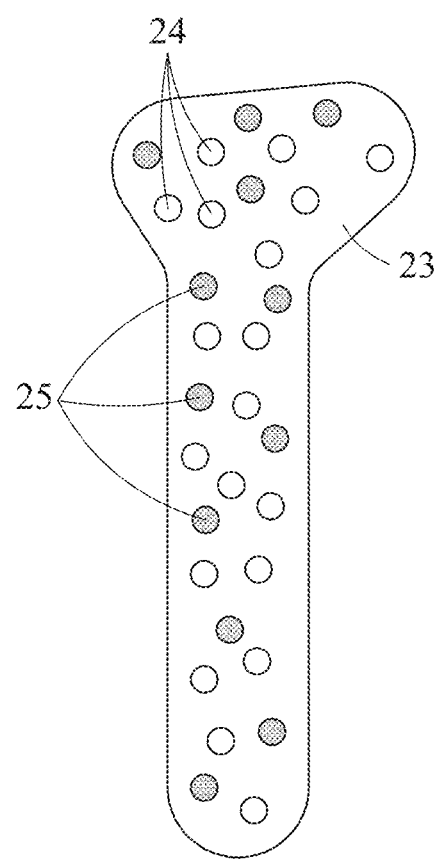
FIG. 16 is a top view illustrating a base, a plurality of pressure sensors, and a plurality of vibrators according to at least one example embodiment.

FIG. 16 is a top view illustrating a base, a plurality of pressure sensors, and a plurality of vibrators according to at least one example embodiment.

Referring to FIG. 16, a plurality of pressure sensors 24 and a plurality of vibrator 25 may be distributed all over a support layer 23. A controller (not shown) may determine a COP based on a pressure distribution measured by the plurality of pressure sensors 24, may determine a positional relationship between the determined COP and a set (or, alternatively, a preset) setting point, and may individually control intensity of vibration of each of the plurality of vibrators 25 based on the determined positional relationship. The setting point may be updated in real time.

For example, when the COP is positioned forward of the setting point, the controller may control, among the plurality of vibrators 25, intensity of vibration of a vibrator provided at the rear of the setting point to be greater than that of a vibrator provided at the front of the setting point. In this manner, it is possible to enhance a sensitivity of a rearfoot of the user and to make the COP move backward.

Figure 17:
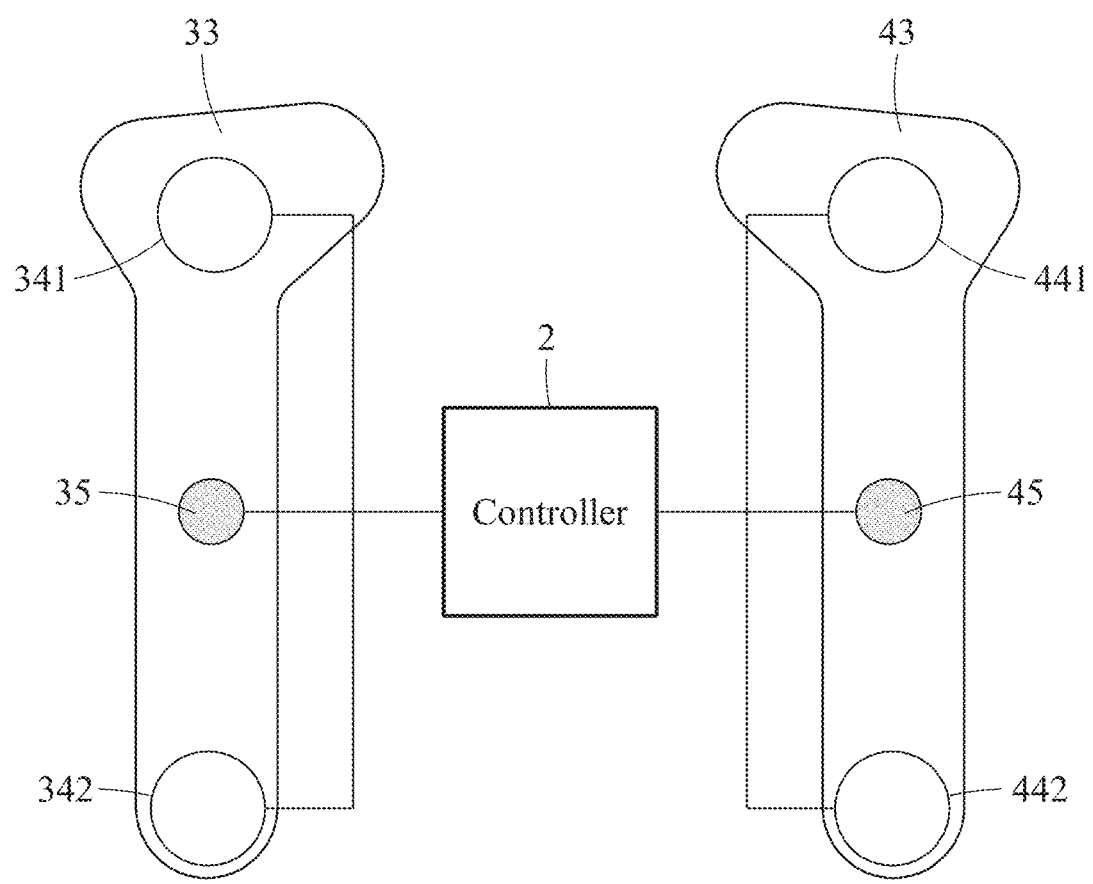
FIG. 17 illustrates a balance enhancement device according to at least one example embodiment.

FIG. 17 illustrates a balance enhancement device according to at least one example embodiment.

Referring to FIG. 17, the balance enhancement device may include a left smart insole, a right smart insole, and a controller 2 configured to control the left smart insole and the right smart insole.

The left smart insole may include a left support layer 33 configured to support a left foot of a user, left pressure sensors 341 and 342 provided to the left support layer 33, and a left vibrator 35 provided to the left support layer 33. The left pressure sensors 341 and 342 may sense a pressure applied from the left foot of the user. The left pressure sensors 341 and 342 may include the left front pressure sensor 341 configured to overlap a forefoot of the left foot of the user and the left rear pressure sensor 342 configured to overlap a rearfoot of the left foot of the user.

The right smart insole may include a right support layer 43 configured to support a right foot of the user, right pressure sensors 441 and 442 provided to the right support layer 43, and a right vibrator 45 provided to the right support layer 43. The right pressure sensors 441 and 442 may sense a pressure applied from the right foot of the user. The right pressure sensors 441 and 442 may include the right front pressure sensor 441 configured to overlap a forefoot of the right foot of the user and the right rear pressure sensor 442 configured to overlap a rearfoot of the right foot of the user.

The controller 2 may include processing circuitry including, but is not limited to, a central processing unit (CPU), an arithmetic logic unit (ALU), a digital signal processor, a microcomputer, a field programmable gate array (FPGA), a programmable logic unit, a microprocessor, application-specific integrated circuit (ASIC), etc. The processing circuitry of controller 2 may execute instructions that configure the processing circuitry as special purpose processing circuitry to compare the pressure measured by the left pressure sensors 341 and 342 and the pressure measured by the right pressure sensors 441 and 442, and may adjust intensity of vibration of the left vibrator 35 and the right vibrator 45. For example, if a pressure value measured by the left pressure sensors 341 and 342 is greater than a pressure value measured by the right pressure sensors 441 and 442, the controller 2 may control the left vibrator 35 and the right vibrator 45 such that the intensity of vibration of the right vibrator 45 may be greater than that of the left vibrator 35. In this case, the sensitivity of the right foot of the user may be relatively enhanced and a center of gravity of the user may move to the right foot. Accordingly, a magnitude of pressure measured by the left pressure sensors 341 and 342 may decrease and a magnitude of pressure measured by the right pressure sensors 441 and 442 may increase. A difference between the pressure measured by the left pressure sensors 341 and 342 and the pressure measured by the right pressure sensors 441 and 442 may decrease.

While FIG. 17 illustrates a single left vibrator 35 and a single right vibrator 45, example embodiments are not limited thereto. For example, each of the left vibrator 35 and the right vibrator may include the two front vibrators 151 and the rear vibrator 152.

Further, in addition to the common controller 2, the left smart insole and the right smart insole may each include their own respective controller 16 configured to communicate with the common controller 2.

A number of example embodiments have been described above. Nevertheless, it should be understood that various modifications may be made to these example embodiments. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A smart insole configured to be worn by a user, the smart insole comprising:
a support layer;
a plurality of pressure sensors associated with the support layer, the plurality of pressure sensors configured to sense a pressure applied thereto by a foot of the user;
a plurality of vibrators associated with the support layer, the plurality of vibrators configured to generate a vibration; and
a controller configured to, determine a center of pressure (COP) of the foot of the user based on the pressure sensed by each of the plurality of pressure sensors, determine a positional relationship between a setting point and the COP, determine whether the COP is skewed in a first direction from the setting point based on the positional relationship between the setting point and the COP, and control the plurality of vibrators based on the positional relationship between the setting point and the COP by setting an intensity of the vibration in the first direction relative to the setting point stronger than the intensity of the vibration in a second direction opposite the first direction, in response to the controller determining that the COP is skewed in the first direction from the setting point.

2. The smart insole of claim 1, wherein the plurality of vibrators is configured to generate the vibration such that the intensity of the vibration is less than a set frequency.

3. The smart insole of claim 1, wherein the controller is configured to control the plurality of vibrators based on information on at least one of a distance from the COP to the setting point and a direction from the COP toward the setting point.

4. The smart insole of claim 3, wherein the controller is configured to control the plurality of vibrators such that, among the plurality of vibrators, an intensity of the vibration rearward of the setting point is greater than that of an intensity of the vibration provided forward of the setting point, in response to the controller determining that the COP is in front of the setting point.

5. The smart insole of claim 4, wherein the controller is configured to control the plurality of vibrators such that ones of the plurality of vibrators rearward of the setting point vibrate and ones of the plurality of vibrators forward of the setting point do not vibrate, in response to the controller determining that the COP is in front of the setting point.

6. The smart insole of claim 4, wherein the controller is configured to, determine whether a distance from a first auxiliary line to the COP is greater than or equal to a first threshold distance, the first auxiliary line being perpendicular to a longitudinal direction of the support layer and intersecting the setting point, and determine that the COP is positioned at the front of the setting point, if the distance from the first auxiliary line to the COP is greater than or equal to the first threshold distance and the COP is positioned at the front of the setting point.

7. The smart insole of claim 3, wherein the controller is configured to control the plurality of vibrators such that, among the plurality of vibrators, an intensity of the vibration on a right side of the setting point is greater than an intensity of the vibration on a left side of the setting point, in response to the controller determining that the COP is on the left side of the setting point.

8. The smart insole of claim 7, wherein the controller is configured to control the plurality of vibrators such that ones of the plurality of vibrators on the right side of the setting point vibrate and ones of the plurality of vibrators on the left side of the setting point do not vibrate, in response to the controller determining that the COP is on the left side of the setting point.

9. The smart insole of claim 7, wherein the controller is configured to, determine whether a distance from a second auxiliary line is greater than or equal to a second setting threshold, the second auxiliary line being parallel to a longitudinal direction of the support layer and intersecting the setting point to the COP, and determine that the COP is positioned on the left side of the setting point, if the distance from the second auxiliary line is greater than or equal to the second setting threshold and the COP is positioned at the left side of the setting point.

10. The smart insole of claim 1, wherein the plurality of vibrators comprises:

a front vibrator configured to apply a vibration to a forefoot of the user; and a rear vibrator configured to apply a vibration to a rearfoot of the user.

11. The smart insole of claim 10, wherein the controller is configured to vibrate one or more of the front vibrator and the rear vibrator based on the positional relationship between the setting point and the COP.

12. The smart insole of claim 10, wherein the front vibrator comprises:

a right front vibrator and a left front vibrator that are aligned in a width direction of the support layer, and wherein the controller is configured to control plurality of vibrators such that the right front vibrator vibrates and the left front vibrator does not vibrate, in response to the controller determining that the COP is positioned on a left side of the setting point.

13. The smart insole of claim 1, further comprising:

a base configured to support the support layer; and a cover detachably provided to the base, wherein support layer is provided between the base and the cover.

14. A smart insole configured to be worn by a user, the smart insole comprising:

a support layer;

a plurality of pressure sensors associated with the support layer, the plurality of pressure sensors configured to sense a pressure applied thereto by a foot of the user;

a plurality of vibrators associated with the support layer, the plurality of vibrators configured to generate a vibration having an intensity less than a set frequency; and a controller configured to, determine a center of pressure (COP) of the foot of the user based on the pressure sensed by each of the plurality of pressure sensors, determine whether the user is in an abnormal condition of balance based on a positional relationship between a setting point and the COP such that the user is determined to be in the abnormal condition of balance in response to the positional relationship between the setting point and the COP indicating that the COP is skewed in a first direction from the setting point, and control the plurality of vibrators such that the intensity of the vibration is different in at least a portion of the plurality of vibrators by setting the intensity of the vibration in the first direction relative to the setting point stronger than the intensity of the vibration on a second direction opposite the first direction, in response to the controller determining that the COP is skewed in the first direction from the setting point.

15. The smart insole of claim 14, wherein the controller is configured to, determine that the user is in the abnormal condition of balance in response to the controller determining that the COP is in front of or behind the setting point, and control the plurality of vibrators such that, among the plurality of vibrators, the intensity of the vibration forward of the setting point differs from the intensity of the vibration rearward of the setting point, in response to the controller determining that the COP is in front of or behind the setting point.

16. The smart insole of claim 15, wherein the controller is configured to, determine that the user is in the abnormal condition of balance in response to the controller determining that the COP is on a left side or on a right side of the setting point, and control the plurality of vibrators such that, among the plurality of vibrators, the intensity of the vibration on the left side of the setting point differs from the intensity of the vibration on the right side of the setting point in response to the controller determining that the COP is on the left side or on the right side of the setting point.

17. A balance enhancement device comprising:

a left smart insole including a left support layer configured to support a left foot of a user, the left support layer having at least one left pressure sensor and at least one left vibrator associated therewith;

a right smart insole including a right support layer configured to support a right foot of the user, the right support layer having at least one right pressure sensor and at least one right vibrator associated therewith; and a controller configured to, determine whether pressure values measured by one of the at least one left pressure sensor and the at least one right pressure sensor indicate that pressure is skewed towards the left smart insole or the right smart insole, and control the at least one left vibrator and the at least one right vibrator based on the pressure values measured by the left pressure sensor and the right pressure sensor such that an intensity of a vibration generated by the one the left smart insole or the right smart insole that the pressure is skewed towards is greater than an intensity of a vibration generated by another one of the left smart insole or the right smart insole.

18. The balance enhancement device of claim 17, wherein the controller is configured to control the at least one left vibrator and the at least one right vibrator such that the at least one right vibrator vibrates and the left at least one vibrator does not vibrate, in response to the controller determining that the pressure value measured by the left pressure sensor is greater than the pressure value measured by the right pressure sensor.

19. The balance enhancement device of claim 17, wherein the at least one left vibrator and the at least one right vibrator are configured to generate the vibration such that the intensity of the vibration is less than a set frequency.

\* \* \* \* \*